(12) United States Patent
Buehler et al.

(10) Patent No.: US 6,432,442 B1
(45) Date of Patent: Aug. 13, 2002

(54) CHEWABLE PRODUCT

(75) Inventors: Gail K. Buehler, Lower Gwynedd, PA (US); Frank Bunick, Randolph, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 09/027,629

(22) Filed: Feb. 23, 1998

(51) Int. Cl.⁷ .............................. A61K 9/10; A61K 9/20; A61K 47/38; A61K 47/42
(52) U.S. Cl. ....................................... 424/441; 424/488
(58) Field of Search ............................ 424/488, 439, 424/441, 465; 426/2; 514/944

(56) References Cited

U.S. PATENT DOCUMENTS

| | | | | |
|---|---|---|---|---|
| 4,327,076 A | | 4/1982 | Puglia et al. | |
| 4,439,453 A | | 3/1984 | Vogel | |
| 4,609,543 A | | 9/1986 | Morris et al. | |
| 4,747,881 A | | 5/1988 | Shaw et al. | 106/209 |
| 4,767,789 A | | 8/1988 | Blank et al. | |
| 4,774,091 A | | 9/1988 | Yamahira et al. | |
| 4,778,676 A | | 10/1988 | Yang et al. | 424/79 |
| 4,790,991 A | | 12/1988 | Shaw et al. | 424/441 |
| 4,818,539 A | | 4/1989 | Shaw et al. | 424/441 |
| 4,837,255 A | | 6/1989 | Dechow | 524/23 |
| 4,843,098 A | | 6/1989 | Shaw et al. | 514/778 |
| 4,849,141 A | | 7/1989 | Fujioka et al. | |
| 4,851,392 A | | 7/1989 | Shaw et al. | 514/53 |
| 4,855,134 A | | 8/1989 | Yamahira et al. | |
| 4,857,331 A | | 8/1989 | Shaw et al. | 424/440 |
| 4,879,108 A | | 11/1989 | Yang et al. | 424/440 |
| 4,882,151 A | | 11/1989 | Yang et al. | 424/440 |
| 4,882,152 A | | 11/1989 | Yang et al. | 424/440 |
| 4,882,153 A | | 11/1989 | Yang et al. | 424/440 |
| 4,882,154 A | | 11/1989 | Yang et al. | 424/440 |
| 4,882,155 A | | 11/1989 | Yang et al. | 424/440 |
| 4,882,156 A | | 11/1989 | Yang et al. | 424/440 |
| 4,882,157 A | | 11/1989 | Yang et al. | 424/440 |
| 4,882,158 A | | 11/1989 | Yang et al. | 424/440 |
| 4,882,159 A | | 11/1989 | Yang et al. | 424/440 |
| 4,882,160 A | | 11/1989 | Yang et al. | 424/440 |
| 4,940,587 A | * | 7/1990 | Jenkins et al. | |
| 5,021,241 A | | 6/1991 | Yamahira et al. | |
| 5,039,540 A | | 8/1991 | Ecanow | |
| 5,049,394 A | * | 9/1991 | Howard et al. | |
| 5,229,164 A | | 7/1993 | Pins et al. | 427/3 |
| 5,284,662 A | * | 2/1994 | Koparkar et al. | |
| 5,322,694 A | * | 6/1994 | Sixsmith | |
| 5,489,436 A | | 2/1996 | Hoy et al. | |
| 5,501,861 A | | 3/1996 | Makino et al. | 424/464 |
| 5,576,306 A | * | 11/1996 | Dressman et al. | |
| 5,587,180 A | | 12/1996 | Allen, Jr. et al. | 424/499 |
| 5,595,761 A | | 1/1997 | Allen, Jr. et al. | 424/484 |
| 5,635,210 A | | 6/1997 | Allen, Jr. et al. | 424/465 |
| 5,720,974 A | | 2/1998 | Makino et al. | 424/464 |
| 5,723,143 A | * | 3/1998 | Jacques et al. | |
| 5,776,491 A | | 7/1998 | Allen, Jr. et al. | 424/465 |
| 5,789,393 A | | 8/1998 | Dressman et al. | 514/57 |
| 5,807,576 A | | 9/1998 | Allen, Jr. et al. | 424/465 |
| 5,928,664 A | | 7/1999 | Yang et al. | 424/440 |

FOREIGN PATENT DOCUMENTS

| | | | |
|---|---|---|---|
| EP | 0 139 286 A2 | 10/1984 | |
| EP | 0 190 826 A2 | 8/1986 | ............ A61K/9/16 |
| EP | 0 227 603 A2 | 7/1987 | ............ A61K/9/20 |
| EP | 0 553 777 A2 | 1/1992 | ............ A61K/9/20 |
| EP | 0 502 666 A1 | 9/1992 | ......... A61K/31/715 |
| EP | 0 890 358 A1 | 1/1999 | ............ A61K/9/20 |
| WO | WO 95/20377 | 8/1995 | ............ A61K/9/00 |

* cited by examiner

Primary Examiner—Edward J. Webman

(57) ABSTRACT

The present invention is directed to a gelatin matrix which contains a pharmaceutically active ingredient. In a preferred embodiment, a hydrocolloid is added to the gelatin matrix to improve the physical properties, taste and mouthfeel of the gelatin matrix. A method for making the gelatin matrix containing the hydrocolloid is also disclosed.

10 Claims, No Drawings

CHEWABLE PRODUCT

FIELD OF THE INVENTION

The present invention is directed at a soft, chewable pharmaceutical dosage form. More particularly, the present invention is directed to an oral delivery system for administering a pharmaceutical agent, medicament or other active ingredient by employing a soft, chewable matrix to incorporate the active ingredient.

BACKGROUND OF THE INVENTION

Pharmaceutical and nutritional supplement dosage forms intended for oral administration are typically provided in solid form as tablets, capsules, pills, lozenges, or granules. The tablet form is swallowed whole, chewed in the mouth, or dissolved sublingually. Absorption of the active moiety depends upon its release from the dosage form and may be controlled by several different technologies.

Chewable systems are often employed in the administration of pharmaceuticals, where it is impractical to provide a tablet for swallowing whole. The act of chewing helps to break up the tablet particles as the tablet disintegrates and may increase the rate of absorption by the digestive tract. Chewable systems are also advantageous where it is desirable to make an active ingredient available topically in the mouth or throat for both local effects or systemic absorption. Chewable dosage forms are also utilized to improve drug administration in pediatric and geriatric patients.

Palatability and "mouthfeel" are important characteristics to be considered in providing a dosage form, or matrix, for an active pharmaceutical medicament. Unfortunately, many pharmaceuticals and other active ingredients have a bitter or otherwise unpalatable taste, or an unacceptable mouthfeel, due to the grittiness or chalkiness of the compound, or both. These characteristics make it difficult to prepare acceptable dosage forms using the current state of the art for chewable dosage forms, since the objectionable taste and/or mouthfeel make it less likely to obtain compliance by the user.

As a result, several approaches have been tried in attempting to overcome these problems. The poor taste of a pharmaceutical or other active ingredient may be masked by using suitable flavoring compounds, and/or sweeteners. Encapsulation of the active ingredient may also serve to mask bitterness and other undesirable tastes. These approaches do not effect the physical state of the dosage from currently employed in the art. For example, chewable vitamin tablets are typically prepared as a compressed tablet, incorporating one or more active ingredients (e.g., vitamins), a sweetener and flavoring agent to mask the taste of the active ingredient, and a binder, typically microcrystalline cellulose.

Generally, chewable tablets are made by direct compression of a mixture of tabulating compounds including the active ingredient, flavoring, binders, etc. The mixture is fed into a die cavity of a tablet press and a tablet is formed by applying pressure. Hardness of the resulting tablet is a direct function of the compression pressure employed. A softer tablet, having an easier bite-through, may be prepared by adding a disintegrant, such as alginic acid, to the tablet mix. Alternatively, a softer tablet may be formed by employing reduced compression pressures. In either case, the resulting tablet is softer, fragile, brittle, and easily chipped.

Attempts have been made to reduce the grittiness and/or chalkiness of the compressed tablet by coating particles of the active ingredient with oils or fats prior to incorporation into the delivery system. See U.S. Pat. Nos. 4,327,076 and 4,609,543, incorporated herein by reference. In this way, the grittiness or chalkiness of the particles in the mouth is reduced. After swallowing, the oil or fat is digested and the drug particle can dissolve in the gastric contents. However, the addition of particles coated with fats or oils to the tablet mix can decrease the binding of the tableting ingredients and cause a reduction in the tablet hardness.

Other techniques for providing a chewable delivery system involve the use of a gum base. Gum bases are insoluble elastomers which form the essential element for chewing gum. The gum base is typically blended with one or more sweeteners to obtain a confectionery gum. A coating containing the active ingredient is then applied over the confectionery gum. As the dosage form is chewed, the coating fractures and/or dissolves in the mouth and is swallowed. Despite these disclosures there is an ongoing need for a chewable delivery system, particularly for children, which is pleasant tasting and preferably in a form which is easy to chew and swallow.

SUMMARY OF THE INVENTION

The present invention provides a chewable, gelatin based matrix which contains pharmaceutically active ingredients. More particularly, the present invention provides gelatin based matrices that can be chewed and swallowed easily. In preferred embodiments of the invention, hydrocolloid ingredients are added to the gelatin matrix in order to enhance the physical properties of the gelatin matrix and increase the user acceptance. The addition of a hydrocolloid to the gelatin typically reduces the rubbery nature of the gelatin, improves the mold release characteristics, decreases sticking to the teeth, improves the mouthfeel, and improves the ability to chew and swallow the product in the desired period of time.

DETAILED DESCRIPTION OF THE INVENTION

The gelatin used in the present invention is selected from a wide variety of sources that are pharmaceutically acceptable types, including gelatin-glycerin, pure gelatin, or sugar gelatins. These and other suitable gelatins are disclosed in *Remington's Practice of Pharmacy*, Martin & Cook, 17th edition, p. 1298. The level of gelatin used in the present invention typically comprises from about 1 to about 20 weight percent, preferably from about 3 to about 15 and most preferably from about 4 to about 10 weight percent on a dry solids basis. Typically, the gelatin is employed in combination with hydrocolloid such that the gelatin/hydrocolloid is up to about 40 weight percent, generally from about 2 to about 30 weight percent, and preferably from about 6 to about 20 weight percent on a dry solids basis. In a highly preferred embodiment the hydrocolloid is about 10 weight percent on a dry solids basis of the gel-forming matrix.

The level of gelatin employed in the invention is related to bloom strength. Those with skill in the art will recognize that bloom strength is a measure of the gelling property of a particular gelatin, with higher bloom strengths relating to the ability of the gelatin to more strongly crosslink at an equal concentration of gelatin. The bloom strengths of the gelatins employed in the present invention are from about 150 to about 350 with a preferred value of about 250. A bloom strength of about 250 provides the proper mouthfeel, texture and chewing characteristics to the gelatin matrix of the invention.

In preferred embodiments of the invention, hydrocolloids are added to the gelatin matrix in order to improve the properties of the gelatin matrix. As used herein, hydrocolloid is understood to mean any water soluble material that swells when contacted with water. Suitable hydrocolloids include natural and modified gums, cellulosics, modified cellulosics, pectins, mucillages, modified starches, noncellulosic polysaccharides, algal polysaccharides and mixtures thereof. More specifically the hydrocolloids include starch, agar-agar, microcrystalline cellulose, methylcellulose, hydroxypropyl cellulose (HPC), hydroxypropyl methylcellulose (HPMC), xanthan gum, carrageenan gum, locust bean gum, alginates, acacia, carboxymethylcellulose (CMC), karaya gum, acacia gum, sodium alginate, sodium CMC, guar gum, tragacanth, mixtures of the hydrocolloids and the like.

When using various hydrocolloid ingredients, various ratios of gelatin/hydrocolloids have been discovered which have been found to possess beneficial mouthfeel, texture and chewing characteristics. For example, when using starch, the weight ratio of from about 1:1.3 to about 1:1.8 possesses desirable characteristics. More preferably the gelatin/starch weight ratio is from 1:1.4 to about 1:1.55 and most preferably the weight ratio is about 1:1.50. When agaragar is used the weight ratio is about 1:0.35 to about 1: 1.5, preferably from 1:0.6 to about 1:1.2, and most preferably about 1:0.75. When employing hydroxypropylcellulose the ratio is from about 1:0.2 to about 1:0.8, preferably the HPC/starch weight ratio is from about 1:0.3 to about 1:0.6 and most preferably the weight ratio is about 1:0.45. Those with skill in the art will recognize that other hydrocolloids can be used in combination with the specified hydrocolloids in the ratios specified, i.e., a mixture of two or more hydrocolloids, without departing from the present invention.

The present invention incorporates an effective amount of the pharmaceutically active ingredient in the gelatin matrix. Typically the pharmaceutically active ingredient is employed in the gelatin matrix at a level depending on the dosage strength desired and the particular active used. Suitable categories of pharmaceutically acceptable materials that may be employed in the present invention include any stable drug/excipient combination. Illustrative categories and specific examples include antitussives, such as dextromethorphan, dextromethorphan hydrobromide, noscapine, carbetapentane citrate, and chlophedianol hydrochloride; antihistamines, such as chlorpheniramine maleate, phenindamine tartrate, pyrilamine maleate, doxylamine succinate, and phenyltoloxamine citrate; decongestants, such as phenylephrine hydrochloride, phenylpropanolamine hydrochloride, pseudoephedrine, hydrochloride ephedrine; alkaloids, such as codeine phosphate, codeine sulfate and morphine; mineral supplements such as potassium chloride and calcium carbonates, magnesium oxide, and other alkali metal and alkali earth metal salts; laxatives, antacids; ion exchange resins such as cholestyramine; anti-cholesterolemic and anti-lipid agents such as gemfibrozil; $H_2$ antagonists such as famotidine; antiarrhythmics such as N-acetyl-procainamide; antipyretics and analgesics such as acetaminophen, aspirin, ibuprofen and naproxen; appetite suppressant such as phenylpropanolamine hydrochloride or caffeine; expectorants such as guaifenesin; antibiotics such as penicillin, cephalosporins and macrolide antibiotics; oral nitrates such as isosorbide dinitrate, isosobide mononitrate, and nitroglycerin; and vitamins, alone or in combination, as multi-vitamins, antioxidants, herbal medicaments such as melatonin, cholestin, goldenrod, garlics, St. John's wort and other DSHEA (dietary supplement health and safety act) ingredients or compounds. Additional useful active medicaments include anti-inflammatory substances, coronary dilators, cerebral dilators, peripheral vasodilators, anti-infectives psychotropics, antimanics, stimulants, gastrointestinal sedatives, anti-diarrheal preparations, anti-anginal drugs, vasodilators, anti-hypertensive drugs, vasoconstrictors and migraine treatments, antibiotics, tranquilizers, antipsychotics, antitumor drugs, anticoagulants and antithrombotic drugs, hypnotics, sedatives antiemetics, antinauseants, anticonvulsants, neuromuscular drugs, hyper and hypoallergenic agents, thyroid and antithyroid preparations, diuretics, antispasmodics, uterine relaxants, nutritional additives, antiobesity drugs, anabolic drugs, erythropoietic drugs, antiasthmatic, cough suppressants, mucolytics, anti-uricemic drugs, and the like. Mixtures of the drug and medicaments may also be used. The dry solids weight basis of the pharmaceutically active ingredients is typically from about 2 to about 30 weight percent, preferably from about 5 to about 15 weight percent and most preferably about 10 weight percent.

The pharmaceutically active ingredients may be in solid or liquid form. In a highly preferred embodiment the pharmaceutically active ingredient is preferably coated or encapsulated with materials appropriate to survive temperature and water for processing and stability. This allows the gelatin mixture to be chewed while simultaneously taste-masking the drug or medicament. Suitable taste-masking technologies are known in the art, and include cellulose acetate, cellulose acetate butyrate, polyvinylpyrrolidone, hydroxymethylcellulose, dimethylamino methacrylate, cellulose triacetate and 2-vinyl pyridine. Especially preferred are the cellulose esters and methyl methacrylate coatings set forth in U.S. Pat. No. 5,489,436, hereby incorporated by reference.

The chewable, solid matrices of the present invention have a texture and hardness such that the matrix is chewed and swallowed in less than about 20 seconds, preferably in less than about 15 seconds and most preferably less than about 10 seconds. While the matrices of the present invention are rapidly chewed and swallowed, the texture of the matrices are such that they do not appreciably dissolve in the mouth in the times recited above. More specifically, the matrices have a texture such that they must be chewed.

One advantage of the present invention is that the gelatin matrix has a texture and mouthfeel similar to candy, the matrix is soft and is easily chewed and swallowed, particularly by children. Testing of the dosage form with children has indicated that children prefer this form and it is expected that because children prefer the gelatin matrix they will more readily take the drugs at the prescribed intervals and will also complete the prescribed treatments.

Without wishing to be bound by any theory, it is believed that the reason why the gelatin matrix is preferred, particularly by children, is because of its pleasant taste properties and soft moist texture. Since the matrix is soft and readily chewed, the drug remains within gelatin fragments, sequestered in the gelatin matrix. Because the drug is sequestered in the gelatin matrix, the unpleasant drug taste in the mouth is reduced. It is believed that the addition of the hydrocolloids to the gelatin matrix decreases the chewiness of the gelatin matrix, resulting in enhanced texture, break-up in the mouth, softness and mouthfeel. The present invention provides a convenient dosage form, particularly for children.

If the gelatin matrix is too chewy, the drug will have sufficient time to dissolve because it remains in the mouth for a longer period of time, and the unpleasant taste associated with drugs will become apparent to the user. Also if the drug is provided in an encapsulated form, an excessive amount of chewing will increase the likelihood that the drug coating will be broken or breached. This breaking of the coating will also increase the likelihood that the taste of the drug will become apparent to the user.

The other major ingredients used in the present invention are water, sugar or sugar-substitutes. Since the present invention provides a candy-like product, a large percentage of the final product is made up of sweeteners such as sugar, corn syrup, maltodextrose, polydextrose, ISOMALT as well as mixtures thereof. Artificial sweeteners known in the art, including saccharin, aspartame and Acesulfame-K, may also be used. Preferably a combination of sugar and artificial sweeteners are used in the present invention. Sweetener levels can be as high as about 60 weight percent dry solids, but more typically is from about 30 to about 50 weight percent.

Water is used to hydrate both the gelatin and hydrocolloid, and makes up the remainder of the dry product weight. Water is present in the final product at levels of from about 10 to 30 weight percent, more typically, water is present at a level at about 20 to about 25 weight percent.

For dietary and health reasons it may be desirable to provide a sugarless formulation in which the sweeteners are be replaced with polyhydric alcohols and mixtures of these alcohols, including but not limited to, sorbitol, xylitol, erythritol, maltitol and the like.

The present invention is preferably prepared by the following method. Gelatin is added to water at approximately 100° C. to hydrate the gelatin, then maintaining the hydrated gelatin at a temperature of about 60 to about 70° C. If a hydrocolloid is employed, the hydrocolloid is hydrated, also preferably while being heated to above boiling temperature in a separate container along with the soluble solids such as sugar and corn syrup. After the water fraction of the hydrocolloid/sugar solids suspension is reduced to desired solids content and cooled down to approximately 90° C., the gelatin solution is added to the hydrocolloid/sugar solids mixture. At a cooler temperature that assures flowability of the mixture without compromising the integrity of the flavorings, it is appropriate to add flavorings, artificial sweeteners, preservatives, colorings, food acids and the like. The pharmaceutically active materials are then added to the mixture. The contents of the mixture are then mixed to achieve a uniform concentration.

In order to form the desired final shape of the matrix, at least three different options are possible. First the mixture could be allowed to cool sufficiently such that the mixture could be extruded and cut into the desired length pieces. Alternatively, the mixture could be deposited in starch molds and then removed from the starch molds by removing the starch from the solidified mixture. In the a preferred method the warm mixture is poured into molds. The molds are preferably coated with a lubricant to aid in the release of the gelatin matrix from the mold. The addition of the hydrocolloid to the gelatin matrix also improves the mold release properties of the gelatin matrices.

The following examples are illustrative of the present invention and are not to be construed to limit the example to the following embodiments. The following commercially available materials were used in the examples that follow. The encapsulated acetaminophen was obtained from Eurand. Gelatin was obtained from SBI, a 250 Bloom value gelatin. Coated acetaminophen was purchased from CPI and the starch used was Amerimaize 2370, (American Maize-Products Company) a high amylose modified food starch. Unless noted otherwise all parts below are reported in dry weight percent. APAP is understood to be acetaminophen.

EXAMPLE 1

Gelatin matrices were prepared by the following method. Water in the bottom of a double boiler pan was heated by use of a hot plate. Purified water was added to a second pan and heated until boiling; a portion of the water was added to the top of the double boiler. The gelatin was sprinkled in and gently stirred and allowed to hydrate for about 30 minutes. In a sauce pan, purified water, sodium benzoate and starch were added and mixed to disperse the starch into a slurry. Corn syrup (dextrose equivalent 43) was added to the starch slurry. With constant stirring, the starch/corn syrup slurry was heated to a boil. While boiling, sucrose was added. When the starch/sugar slurry was cooked down to the desired percent solids, the mixture was allowed to cool down to a suitable temperature at which the gelatin solution was added and mixed well. The following ingredients were then added to the sugar/starch/gelatin mixture: anhydrous citric acid, FD&C Red No. 40, Acesulfame-K (Hoescht-Celanese) and encapsulated acetaminophen. These materials were thoroughly stirred into the mixture. Artificial flavoring was then added to the mixture. The contents of the final product were maintained at 65–75° C. to allow the mixture to remain pourable for deposit.

The mixture was deposited into unit molds treated with a release agent, portioned in the amount to assure dosage strength. The product in the molds was allowed to cool and the molds sealed.

The following formulations were tested to determine which product had the preferred physical properties:

| A) | Gelatin | 9.27% | 1.00:0.00 gelatin/starch ratio |
|---|---|---|---|
| | Starch | 0% | |
| | Sugar Solids | 58.83% | |
| | Encapsulated APAP | 9.44% | |

Remaining Solids to Add up to 80% w/w at Time of Deposit

COMMENTS: Average 28 seconds to chew. Very rubbery and hard chew, slimy, unpleasant, very tough and broke up in chunks in mouth.

| B) | Starch | 4.07% | 1.00:1.04 gelatin/starch ratio |
|---|---|---|---|
| | Gelatin | 3.91% | |
| | Sugar solids | 60.94% | |
| | Encapsulated APAP | 9.36% | |

Remaining Solids to Add up to 80% w/w at Time of Deposit

COMMENTS: Good taste, somewhat sticky.

| C) | Starch | 5.12% | 1.00:1.30 gelatin/starch ratio |
|---|---|---|---|
| | Gelatin | 3.94% | |
| | Sugar solids | 64.51% | |
| | Encapsulated APAP | 4.71% | |

| D) | Starch | 5.32% | 1.00:1.35 gelatin/starch ratio |
|---|---|---|---|
| | Gelatin | 3.93% | |
| | Sugar solids | 59.45% | |
| | Coated APAP | 9.83% | |

Remaining Solids to Add up to 80% w/w at Time of Deposit

COMMENTS: Texture "snotty", somewhat sticky. Needs starch increased for enhanced properties.

| E) | Starch | 5.70% | 1.00:1.46 gelatin/starch ratio |
|---|---|---|---|
| | Gelatin | 3.91% | |
| | Sugar solids | 59.22% | |
| | Coated APAP | 9.72% | |

Remaining Solids to Add up to 80% w/w at Time of Deposit

COMMENTS: Good texture, needs starch level to be increased.

| F) | Starch | 5.80% | 1.00:1.45 gelatin/starch ratio |
|---|---|---|---|
| | Gelatin | 3.99% | |
| | Sugar solids | 60.27% | |
| | Encapsulated APAP | 9.36% | |

Remaining Solids to Add up to 80% w/w at Time of Deposit

COMMENTS: Average 18 seconds to chew. The optimal batch for testing and showing. Good taste and texture, slightly firm, not stick, breaks up in mouth.

| G) | Starch | 5.72% | 1.00:1.46 gelatin/starch ratio |
|---|---|---|---|
| | Gelatin | 3.92% | |
| | Sugar solids | 60.53% | |
| | Encapsulated APAP | 9.25% | |

Remaining Solids to Add up to 80% w/w at Time of Deposit

COMMENTS: Average 18 seconds to chew. Good texture, firm chew, slight elastic, clean bite, breaks up easily. Very similar to "F".

| H) | Starch | 6.15% | 1.00:1.56 gelatin/starch ratio |
|---|---|---|---|
| | Gelatin | 3.94% | |
| | Sugar solids | 63.49% | |
| | Encapsulated APAP | 4.71% | |

Remaining Solids to Add up to 80% w/w at Time of Deposit

COMMENTS: Better texture, more firm (than B).

| I) | Starch | 6.10% | 1.00:1.56 gelatin/starch ratio |
|---|---|---|---|
| | Gelatin | 3.91% | |
| | Sugar solids | 58.44% | |
| | Coated APAP | 9.84% | |

Remaining Solids to Add up to 80% w/w at Time of Deposit

COMMENTS: Little too firm, try reducing starch for this particular formula.

| J) | Starch | 6.98% | 1.00:1.75 gelatin/starch ratio |
|---|---|---|---|
| | Gelatin | 3.99% | |
| | Sugar solids | 59.18% | |
| | Encapsulated APAP | 9.25% | |

Remaining Solids to Add up to 80% w/w at Time of Deposit

COMMENTS: Average 18 seconds to chew. Firmer texture with increased starch over "F". Tender chew, clean, breaks up in mouth, very slightly sticky, not as clean as "G", short bite, some elasticity.

| K) | 100% Starch-No Gelatin | | |
|---|---|---|---|
| | Starch | 9.64% | 0.00:1.00 gelatin/starch ratio |
| | Sugar solids | 60.58% | |
| | Encapsulated APAP | 9.25% | |

Remaining Solids to Add up to 80% w/w at Time of Deposit

COMMENTS: Average 11 seconds to chew. Very sticky on teeth and in mouth and on the mold. No elasticity, very sticky, very gooey, never gelled up.

The above results demonstrate that a gelatin/starch ratio of about 1:1.3 to about 1:1.8 provided a matrix that had an optimal combination of firmness, mouthfeel, minimal stickiness and good texture for providing the coated acetaminophen particles.

EXAMPLE 2

The following formulations were made replacing starch with other hydrocolloids. A similar method to the one described in Example 1 above, was used to prepare the samples.

| A) | Agar-Agar | 2.87% | 1.00:0.73 gelatin/hydrocolloid ratio |
|---|---|---|---|
| | Gelatin | 3.93% | |
| | Sugar solids | 63.36% | |
| | Encapsulated APAP | 9.25% | |

Remaining Solids to Add up to 80% w/w at Time of Deposit

COMMENTS: Average 11 seconds to chew. Firm, very short bite, very clean, aids in the release properties from mold, a "brittle" gel, dry, firm, fragments into pieces upon chewing, unpleasant mouthfeel (at this concentration).

| B) | HPMC | 5.72% | 1.00:1.46 gelatin/hydrocolloid ratio |
|---|---|---|---|
| | Gelatin | 3.92% | |
| | Sugar solids | 60.53% | |
| | Encapsulated APAP | 9.25% | |

Remaining Solids to Add up to 80% w/w at Time of Deposit

COMMENTS: Formula very gooey. Did not release from mold.

| C) | Microcrystalline Cellulose | 2.91% | 1.00:0.43 gelatin/hydrocolloid ratio |
|---|---|---|---|
| | Gelatin | 6.74% | |
| | Sugar solids | 60.47% | |
| | Encapsulated APAP | 9.25% | |

Remaining Solids to Add up to 80% w/w at Time of Deposit
COMMENTS: Average 12 seconds to chew. Slimy feel to touch and mouth. Clean bite, not sticky, nice body, very tender, "Jell-O-like" with a little bounce, easy to chew, not elastic, clean in mouth.

| D) | HPMC | 2.91% | 1.00:0.43 gelatin/hydrocolloid ratio |
|---|---|---|---|
| | Gelatin | 6.74% | |
| | Sugar solids | 60.47% | |
| | Encapsulated APAP | 9.25% | |

Remaining Solids to Add up to 80% w/w at Time of Deposit
COMMENTS: Average 13 seconds to chew. Slightly more firm than Example 1 "G". Tender chew, short bite, clean mouthfeel, a little too tough, very slightly sticky.

| E) | HPC | 2.91% | 1.00:0.43 gelatin/hydrocolloid ratio |
|---|---|---|---|
| | Gelatin | 6.74% | |
| | Sugar solids | 60.47% | |
| | Encapsulated APAP | 9.25% | |

Remaining Solids to Add up to 80% w/w at Time of Deposit.
COMMENTS: Average 13 seconds to chew. Firm, slightly elastic, clean bite, firmer than Example 1 "G".

Example 2 demonstrates that the selection of the hydrocolloid in the gelatin matrix causes the ratio of gelatin/hydrocolloid to vary in order to provide the desired mouthfeel, texture and hardness. The addition of a one or more additional components is expected to also modify the optimal ratio of the gelatin and hydrocolloids.

We claim:
1. A chewable composition comprising:
    a matrix comprising a gelatin and a hydrocolloid, wherein the hydrocolloid is hydroxypropyl cellulose, said matrix further containing from about 2 to about 10 weight percent of a pharmaceutically active ingredient and from about 10 to about 30 weight percent water in the final composition, said matrix being capable of being chewed and swallowed in less than about 20 seconds.
2. The composition of claim 1 wherein the pharmaceutically active ingredient is an analgesic.
3. The composition of claim 2 wherein the analgesic is selected from the group consisting of ibuprofen and acetaminophen.
4. The composition of claim 3 wherein the analgesic is coated.
5. The composition of claim 2 which contains Additionally contains dextromethorphan or pseudoephedrine.
6. A chewable composition comprising:
    a matrix comprising a gelatin and a hydrocolloid, wherein the hydrocolloid comprises hydroxypropylcellulose, and the gelatin/hydroxypropylcellulose weight ratio is from about 1:0.2 to about 1:0.8, the matrix further containing from about 2 to about 10 weight percent of a pharmaceutically active ingredient and from about 10 to about 30 weight percent water in the final composition, the matrix being capable of being chewed and swallowed in less than about 20 seconds.
7. The composition of claim 6 wherein the pharmaceutically active ingredient is an analgesic.
8. The composition of claim 7 wherein the analgesic is selected from the group consisting of ibuprofen and acetaminophen.
9. The composition of claim 7 which additionally contains dextromethorphan or pseudoephedrine.
10. The composition of claim 8 which Additionally contains dextromethorphan or pseudoephedrine.

* * * * *

UNITED STATES PATENT AND TRADEMARK OFFICE
CERTIFICATE OF CORRECTION

PATENT NO.   : 6,432,442 B1                                         Page 1 of 1
DATED        : August 13, 2002
INVENTOR(S)  : Gail K. Buehler and Frank Bunick It is certified that error appears in the above-identified patent and that said Letters Patent is hereby corrected as shown below:

<u>Column 10,</u>
Line 15, please delete the word "contains".
Lines 15 and 35, please delete "A" in the word "additionally" and insert the first letter as -- a --.

Signed and Sealed this

Sixteenth Day of December, 2003

JAMES E. ROGAN
*Director of the United States Patent and Trademark Office*